United States Patent [19]
Nakanishi et al.

[11] Patent Number: 6,096,693
[45] Date of Patent: Aug. 1, 2000

[54] ZINC-MOLYBDENUM-BASED DITHIOCARBAMATE DERIVATIVE, METHOD OF PRODUCING THE SAME, AND LUBRICANT COMPOSITION CONTAINING THE SAME

[75] Inventors: Hiroshi Nakanishi, Saitama; Hiroyuki Iwasaki, Tokyo; Katsuya Koganei, Saitama, all of Japan

[73] Assignee: Tonen Corporation, Saitama, Japan

[21] Appl. No.: 09/256,042

[22] Filed: Feb. 23, 1999

[30] Foreign Application Priority Data

Feb. 28, 1998 [JP] Japan ................................. 10-064217

[51] Int. Cl.[7] ......................... C10M 139/00; C07F 11/00
[52] U.S. Cl. .............................. 508/363; 556/28; 556/31; 556/38; 556/57; 556/118
[58] Field of Search .............................. 508/363; 556/28, 556/31, 38, 57, 118

[56] References Cited

U.S. PATENT DOCUMENTS

| | | |
|---|---|---|
| 3,356,702 | 12/1967 | Farmer et al. . |
| 4,178,258 | 12/1979 | Papay et al. ............................. 508/364 |
| 4,336,148 | 6/1982 | Wirth et al. ............................. 508/136 |
| 4,376,055 | 3/1983 | Korosec et al. ........................ 508/419 |
| 4,428,861 | 1/1984 | Bridger ................................... 508/379 |
| 4,479,883 | 10/1984 | Shaub et al. . |
| 4,559,152 | 12/1985 | Schlicht ................................. 252/42.7 |
| 4,648,985 | 3/1987 | Thorsell et al. ........................ 508/364 |
| 4,705,641 | 11/1987 | Goldblatt et al. ......................... 252/35 |
| 4,730,064 | 3/1988 | Halbert et al. ............................. 508/15 |
| 4,786,423 | 11/1988 | Schroeder .......................... 252/32.7 E |
| 4,812,246 | 3/1989 | Yabe ....................................... 508/364 |
| 4,846,983 | 7/1989 | Ward, Jr. ................................. 252/33.6 |
| 4,849,123 | 7/1989 | Tipton et al. ............................. 252/75 |
| 4,908,143 | 3/1990 | Dumdum et al. ........................ 508/564 |
| 4,915,857 | 4/1990 | Emert et al. ........................ 252/32.7 E |
| 4,938,880 | 7/1990 | Waddoups et al. ...................... 508/364 |
| 4,966,719 | 10/1990 | Coyle et al. ............................. 252/42.7 |
| 4,978,464 | 12/1990 | Coyle et al. ............................. 508/363 |
| 4,992,186 | 2/1991 | Habeeb et al. ........................... 508/364 |
| 4,995,996 | 2/1991 | Coyle et al. ............................. 508/445 |
| 5,019,283 | 5/1991 | Beltzer et al. ........................... 508/279 |
| 5,049,290 | 9/1991 | Emert et al. ........................ 252/32.7 E |
| 5,055,211 | 10/1991 | Habeeb et al. ........................... 508/364 |
| 5,281,347 | 1/1994 | Igarashi et al. . |
| 5,672,572 | 9/1997 | Arai et al. ............................... 508/364 |
| 5,696,063 | 12/1997 | Tokashiki et al. ....................... 508/363 |
| 5,736,491 | 4/1998 | Patel et al. .............................. 508/365 |
| 5,807,813 | 9/1998 | Yamada .................................. 508/363 |
| 5,814,587 | 9/1998 | Vrahopoulou et al. ................. 508/363 |
| 5,824,627 | 10/1998 | McConnachie et al. ............... 508/363 |
| 5,837,657 | 11/1998 | Fang et al. .............................. 508/363 |
| 5,888,945 | 3/1999 | Stiefel et al. ........................... 508/363 |
| 5,895,779 | 4/1999 | Boffa ...................................... 508/555 |
| 5,906,968 | 5/1999 | McConnachie et al. ............... 508/363 |

FOREIGN PATENT DOCUMENTS

| | | | |
|---|---|---|---|
| 0727429 | 8/1996 | European Pat. Off. ........ | C07F 11/00 |
| 0803566 | 10/1997 | European Pat. Off. ..... | C10M 169/04 |
| 62-054359 | 11/1987 | Japan .............................. | C10M 1/26 |
| WO 95/19411 | 7/1995 | WIPO .......................... | C10M 135/18 |

OTHER PUBLICATIONS

"Synthesis of Sulfur–bridged Molybdenum and Tungsten Coordination Compounds", Shibahara, Coordination Chemistry Reviews, 123 (1993), 73–147. month unavailable.

"Effects of Organic Molybdenum Compounds on the Friction and Wear Observed with ZDP–Containing Lubricant Blends", Rounds, Tribology Transactions, vol. 33 (1990), 3, 345–354. month unavailable.

"Effect of Molybdenum Dithiocarbonate and Zinc Dithiophosphate on the Tribological Behavior of $Si_3N_4$ and $Al_2O_3$", Hong, Lubrication Engineering, vol. 50, 8, 616–622, 1994. month unavailable.

*Primary Examiner*—Margaret Medley
*Attorney, Agent, or Firm*—Joseph J. Allocca

[57] ABSTRACT

The present invention is directed to a zinc-molybdenum-based dithiocarbamate derivative which is a complex salt having the metallic components of zinc and molybdenum in the same molecule. When used as a lubricant additive, it imparts a notable friction-reducing effect to the lubricant composition in which it is incorporated, reducing its friction coefficient and improving its stability of friction coefficient at both low and high temperature, particularly at high temperature. In particular, it improves friction-related characteristics much more notably than a combination of a molybdenum and zinc compound.

6 Claims, No Drawings

ZINC-MOLYBDENUM-BASED DITHIOCARBAMATE DERIVATIVE, METHOD OF PRODUCING THE SAME, AND LUBRICANT COMPOSITION CONTAINING THE SAME

BACKGROUND OF THE INVENTION

1. Field of the Invention

This invention relates to a new, oil-soluble zinc-molybdenum-based dithiocarbamate derivative, a method of producing the same, a lubricant additive containing the same as the effective component, and a lubricant composition containing the same, more particularly a new compound having the metallic components of zinc and molybdenum in the same molecule, a method producing the same, a lubricant additive comprising the same, and a lubricant composition containing the same.

2. Prior Art

Recently, energy saving has been promoted in all industrial fields for environmental preservation. In particular, automobile engines are required to reduce friction loss in the engine, because loss of kinetic energy resulting from friction generated in the power transmission system increases fuel consumption.

Reduction in friction loss in the engine has been pursued by improving lubricants, in addition to designs of engines themselves. A number of methods have been proposed to reduce friction by, e.g., decreasing viscosity of the base oil, and use of new friction modifiers, to reduce friction in the boundary lubrication region and thereby to reduce fuel consumption.

For example, sulfurized oxymolybdenum dithiocarbamate has been proposed as a friction modifier, as disclosed by, e.g., U.S. Pat. No. 3,356,702. Compounds which have been used as oilness agent preparations, such as glycerin ester, have been also proposed as friction modifiers, as disclosed by JP Publication No. 62-54359.

However, it has been clarified that sulfurized oxymolybdenum dithiocarbamate, although decreasing friction coefficient to some extent at low temperature, suffers a decreased effect of reducing friction at high temperature seen as an increase in friction coefficient, and that it cannot exhibit the friction-reducing effect sufficiently substanably, even at low temperature, for an equipment required to operate continuously for extended periods.

It is also known that zinc dithiophosphate (ZnDTP) shows a friction-reducing effect, when incorporated in a lubricant. However, there is a requirement to reduce phosphorus content, because phosphoric acid resulting from combustion of the phosphate damages oxidation catalysts in the exhaust gas clean-up system.

Under these circumstances, development of a lubricant composition which exhibits a friction-reducing effect over a wide temperature range has been earnestly demanded, because of widely changing conditions under which an automobile engine, and hence the lubricant therefor, are used.

SUBJECT TO BE SOLVED BY THE INVENTION

It is an object of the present invention to provide a new compound superior to the conventional friction modifier, required for a lubricant which can keep friction coefficient at a low level over a wide temperature range, in particular at high temperature, and exhibit the friction-reducing effect substainably in an engine operating continuously for extended periods.

DECRIPTION OF THE INVENTION

The present invention is directed to a new compound of dithiocarbamate derivative having the metallic components of zinc and molybdenum in the same molecule which shows a notable effect of reducing friction, to a method for producing such material, to the material as a lubricant additive and to a lubricant formulation containing such material.

The first item of the present invention relates to a zinc-molybdenum-based dithiocarbamate derivative represented by formula I:

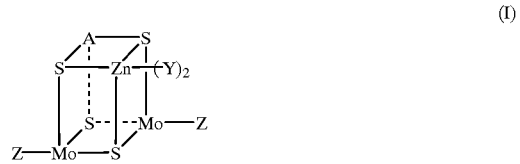

(I)

wherein,

A is Mo—Z or Zn—(—Y)$_2$,

Z in Mo—Z is represented by:

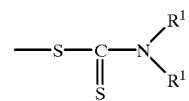

Y in Zn—(—Y)$_2$ is represented by:

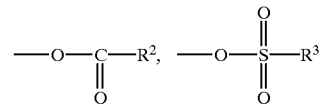

or —SR$^4$, and

R$^1$ to R$^4$ are each a hydrocarbon group having a carbon number of 4 to 30, which may be the same or different.

A particular embodiment of the present invention is a zinc-molybdenum-based dithiocarbamate represented by general formula (I-1)

wherein Y is represented by:

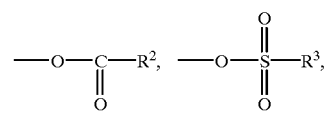

or —SR$^4$, a is 1 or 2, b is 2 or 3, c is 2 or 4, d is 2 when a is 1 or d is 4 when a is 2, and R$^1$, R$^2$, R$^3$, R$^4$ and R$^5$ are each a hydrocarbon group having a carbon number of 4 to 30, which may be the same or different.

The second item of the present invention relates to a method of producing the zinc-molybdenum-based dithiocarbamate derivative represented by formula (1) or (I-1), comprising stages of:

(a) reaction of sulfurized ammonium molybdate (NH$_4$)$_2$MO$_2$S$_{12}$.2H$_2$O or (NH$_4$)$_2$MO$_3$S$_{13}$.2H$_2$O with an alkali metal salt of sulfite and alkali metal salt of dialkyl dithiocarbamate in an aqueous solution, and (b) reaction of the above product with a zinc halide to synthesize $Zn_2Mo_2S_4(dtc)_2X_4$ or $ZnMo_3S_4(dtc)_4X_2$, followed by reaction of the halogen portion of the above product with an alkali metal salt of aliphatic acid, sulfonic acid or alkyl thiol, to form a zinc salt of aliphatic acid, sulfonic acid or alkyl thiol.

The third item of the present invention relates to a lubricant additive comprising the zinc-molybdenum-based dithiocarbamate derivative, represented by formula (I) or (I-1).

The fourth item of the present invention relates to a lubricant composition comprising a lubricant base oil incorporated with the zinc-molybdenum-based dithiocarbamate derivative, represented by formula (I) or (I-1).

PREFERRED EMBODIMENTS OF THE INVENTION

The zinc-molybdenum-based dithiocarbamate derivative of the present invention is a complex salt of polynuclide or molybdenum having the metallic components of zinc and molybdenum in the same molecule, represented by general formula (I):

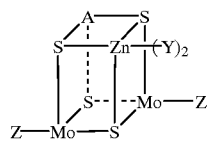
(I)

wherein

A is Mo—Z or Zn—(—Y)$_2$, indicating that either Mo—Z or Zn—(—Y)$_2$ is present in the site A, and wherein:

Z in Mo—Z is represented by:

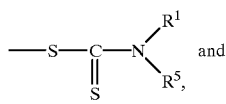
and

Y in Zn—(—Y)$_2$ is represented by:

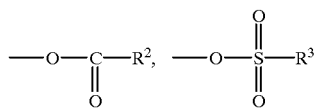

or —SR$^4$, and

R$^1$ to R$^5$ are each a hydrocarbon group having a carbon number of 4 to 30, which may be the same or different.

The hydrocarbon groups useful for the present invention include alkyl having a carbon number of 4 to 30; alkenyl having a carbon number of 4 to 30; and aryl having a carbon number of 6 to 30, which may be substituted by an alkyl group having a carbon number of 1 to 24. An alkyl or alkenyl group having a carbon number of 6 to 20 is particularly preferable for solubility in oil and friction reducing effect. These include straight- or branched-chain alkyl groups, such a hexyl, heptyl, octyl, 2-ethyl hexyl, nonyl, decyl, undecyl, dodecyl, tridecyl, tetradecyl, pentadecyl, hexadecyl, heptadecyl, octadecyl, nonadecyl and eicosyl; and straight- or branched-chain alkenyl groups, such as hexenyl, heptenyl, octenyl, 2-ethyl hexenyl, nonenyl, decenyl, undecenyl, dodecenyl, tridecenyl, tetradecenyl, pentadecenyl, hexadecenyl, octadecenyl, nonadecenyl and eicosenyl. In particular, an alkyl group having a carbon number of 6 to 18 is preferable as R$^1$ and R$^5$, where the two alkyl groups (R$^1$ and R$^5$) may be the same or different. A straight- or branched chain alkyl or alkenyl group is preferable as each of R$^2$ and R$^4$, and an alkyl or alkyl aryl group having a carbon number of 6 to 24 is preferable as R$^3$.

The zinc-molybdenum-based dithiocarbamate derivative, represented by general formula (I) or (I-1), is a dinuclide of Mo when A is Zn—(—Y)$_2$. Examples of the dinuclides include the following compounds:

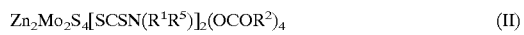
(II)

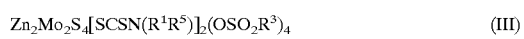
(III)

and

(IV)

More concretely, they include:

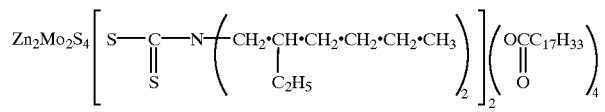
(II-1)

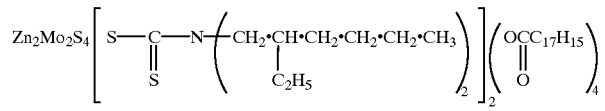
(II-2)

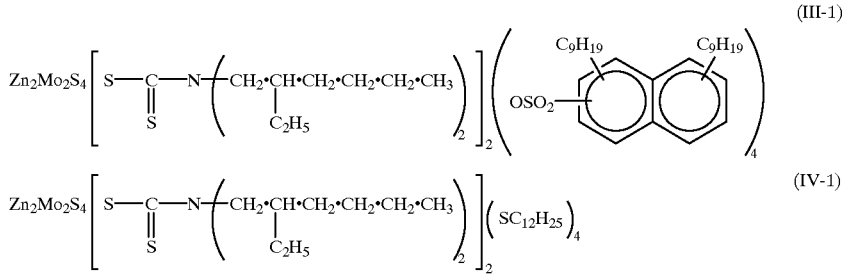

(III-1)

(IV-1)

The zinc-molybdenum-based dithiocarbamate derivative, represented by general formula (I) or (I-1), is a trinuclide of Mo when A is Mo—Z. Examples of the trinuclides include the following compounds:

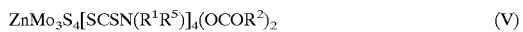 (V)

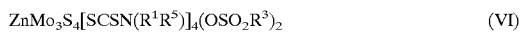 (VI)

and

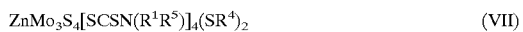 (VII)

More concretely, they include:

of the elements of C, H, O, N and S that constitute each compound are in agreement with the theoretical contents and that Mo/Zn ratio is 1.0, as described later by the examples. The trinuclide is also identified by the elementary analyses for the elements of C, H, O, N and S that constitute the compound, which show that Mo/Zn ratio is 3.0.

The zinc-molybdenum-based dithiocarbamate derivative of the present invention, represented by general formula (I), may be produced, e.g., by the following method:

The zinc-molybdenum-based dithiocarbamate can be produced by a two-stage process involving (1) synthesis of sulfurized molybdenum dialkyl dithiocarbamate, and (2) reaction of the product in the preceding stage with a zinc halide, followed by reaction of the above product with a metal salt of aliphatic acid, sulfuric acid or alkyl thiol.

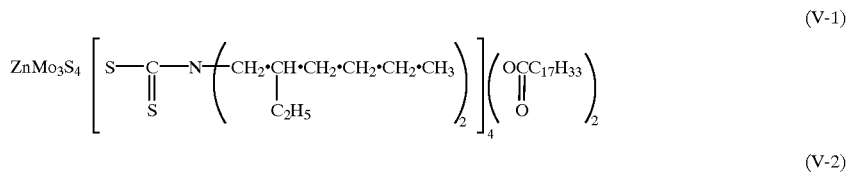

(V-1)

(V-2)

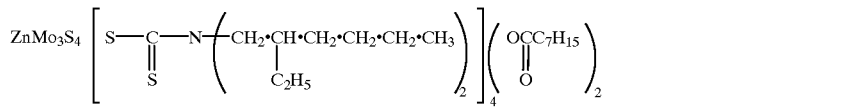

(VI-1)

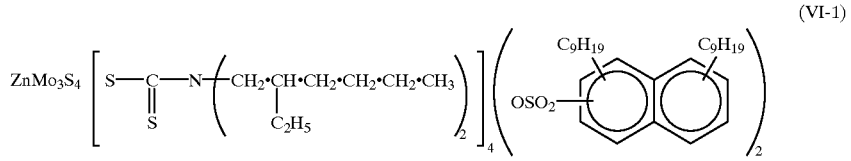

and

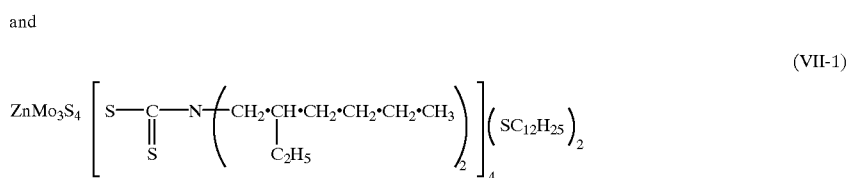

(VII-1)

The zinc-molybdenum-based dithiocarbamate derivative represented by general formula (I) is a complex salt having Zn and Mo in the same molecule, and its structure is identified by the elementary analyses, such as the combustion thermal conductivity method (CARLO ERBA Tester) for C and H, heating IR method for O, Kjeldahl method (in accordance with JIS K-2609) for N, and micro-titration (in accordance with JIS K-2514) and inductively coupled rf plasma emission spectroscopy (ICP, in accordance with JIS K-0116) for S. The dinuclide of Mo is identified by the elementary analyses which show that the observed contents More concretely, the method of the present invention for producing the zinc-molybdenum-based dithiocarbamate derivative comprises two states of: (a) reaction of sulfurized ammonium molybdate $[(NH_4)_2MO_2S_{12}\cdot 2H_2O$ or $(NH_4)_2MO_3S_{13}\cdot 2H_2O]$ with an alkali metal salt of sulfite and alkali metal salt of dialkyl dithiocarbamate in an aqueous solution, and (b) reaction of the above product with a zinc halide (ZnX) to synthesize $Zn_2Mo_2S_4(dtc)_2X_4$ or $ZnMo_3S_4$ $(dtc)_4X_2$, followed by reaction of the halogen (X) portion of the above product with an alkali metal salt of aliphatic acid, sulfonic acid or alkyl thiol, to form a zinc salt of aliphatic acid, sulfonic acid or alkyl thiol. (—SCSN($R^1R^5$) can be used for dtc in the above formulae).

Dinuclide of Mo

The first stage prepares sulfurized molybdenum dialkyl dithiocarbamate [$Mo_2S_4(SCSN(R^1R^5))]_2$ (wherein $R^1$ and $R^5$ are the hydrocarbon groups described earlier] by reacting sulfurized ammonium molybdate [$(NH_4)_2Mo_2S_{12}.2H_2O$] with an alkali metal salt of sulfite and alkali metal salt of dialkyl dithiocarbamate in an aqueous solution. These alkali metal salts are not limited, and those of sodium and potassium can be used. The reaction and operating conditions for the above reaction are not limited, except that it is effected in a nitrogen or argon atmosphere, and can be selected freely. For example, it is possible to produce the objective compound by continuously stirring the reaction system at room temperature.

The second stage reacts the reaction product obtained in the first stage with a zinc halide (ZnX) in a mixed solvent of a halogenated hydrocarbon and aliphatic alcohol, and continues the reaction further by adding an alkali metal salt of aliphatic acid, sulfonic acid or alkyl thiol to the reaction system. Sodium or potassium salt can be freely used as the alkali metal salt. The solvent of halogenated hydrocarbon is not limited, so long as it is serviceable as a solvent for the reaction. Dichloromethane is one of the examples. The solvent of aliphatic alcohol is also not limited, and methanol is one of the examples. Zinc halides useful for the present invention include zinc chloride, fluoride, bromide and iodide. The alkyl thiols useful for the present invention include mercaptan with an alkyl group having a carbon number of 1 to 20. The reaction conditions are not limited, except that the reaction is effected in a nitrogen or argon atmosphere. For example, it can be effected at room temperature.

The above two-stage process gives $Zn_2Mo_2S_4[SCSN(R^1R^5)]_2(OCOR^2)_4$, $Zn_2Mo_2S_4[SCSN(R^1R^5)]_2(OSO_2R^3)_4$ or $Zn_2Mo_2S_4[SCSN(R^1\ R^5)]_2(SR^4)_4$ as the objective compound at a high purity and high yield of approximately 70% or higher.

It is confirmed by various analyses such as elementary and ICP analyses that the reaction product thus produced is a new compound composed of a complex salt containing zinc and molybdenum in the same molecule, as described earlier.

Trinuclide of Mo

The trinuclide of Mo can be produced by the same manner as that used for producing the dinuclide, except that sulfurized ammonium molybdate $(NH_4)_2Mo_3S_{13}.2H_2O$ is used as the starting material. $(NH_4)_2Mo_3S_{13}.2H_2O$ is reacted with an alkali metal salt of sulfite and alkali metal salt dialkyl dithiocarbamate, to prepare $Mo_3S_4[SCSN(R^1R^5)]_4$, which is reacted with a zinc halide, and then with an alkali metal salt of aliphatic acid, sulfonic acid or alkyl thiol, to form:

$Zn_2Mo_3S_4[SCSN(R^1R^5)]_4(OCOR^2)_2$,
$Zn_2Mo_3S_4[SCSN(R^1R^5)]_4(OSO_2R^3)_2$, or
$Zn_2Mo_3S_4[SCSN(R^1\ R^5)]_4(SR^4)_2$.

The trinuclide can be produced, as is the case with the dinuclide, at a high purity and high yield of approximately 70% or higher.

The starting materials of sulfurized ammonium molybdate $(NH_4)_2Mo_2S_{12}.2H_2O$ and $(NH_4)_2Mo_3S_{13}.2H_2O$ can be synthesized by the method proposed by A. Muller et al (Chemistry Uses Molybdenum Proceeding International Conference, 1979-3.59).

The zinc-molybdenum-based dithiocarbamate derivative of the present invention is also useful as a lubricant additive. In particular, it can be used as a friction modifier, antiwear agent, extreme pressure agent and oxidation inhibitor. Of these, it is particularly useful as a friction modifier which shows a notable friction-reducing effect at high temperature. It is also useful as an oxidation inhibitor for various fuels, beginning with gasoline and middle distillates. As the additive, the zinc-molybdenum-based dithiocarbamate derivative represented by general formula (I) can be used after being appropriately dilute with a solvent, such as mineral oil, or as a component for an additive package comprising one or more other additives.

Lubricant base oil to be incorporated with the lubricant composition of the present invention is not limited, and can be selected adequately for specific purposes. Some typical examples of the base oil include mineral, synthetic and vegetable oil.

Mineral base oil includes a lubricant fraction of vacuum distillate of an atmospheric residuum from paraffin, intermediate or naphthenic crude, which is treated by various refining processes, including solvent refining, hydrocracking, hydrotreating, hydrofinishing, solvent dewaxing, catalytic dewaxing, clay treatment, and a combination thereof; vacuum residuum which is treated by solvent-dewaxing and then by one or more of the above refining processes; isomerization-treated wax; and a combination thereof. Aromatic solvents, such as phenol, furfural and N-methyl-2-pyrolidone, are used for solvent refining, and liquefied propane and MEK/toluene are used for solvent dewaxing. Catalytic dewaxing may use shape-selective zeolite as the catalyst component. Base oil contains a limited quantity of aromatic hydrocarbon, 10% or lower as determined by the n-d-m method, especially for oxidation stability, and such oil includes raffinate from solvent extraction and hydrogenated oil. Preferable base oil includes hydrocracked or hydrotreated stock containing aromatic hydrocarbon at 5% or lower, particularly preferably 2% or lower.

Synthetic base oil includes polyα-olefin oligomer (e.g., poly(1-hexene), poly(1-octene), poly(1-decene) or the like, and a mixture hereof), polybutene, alkyl benzene (e.g., dodecyl benzene, tetradecyl benzene, di(2-ethylhexyl) benzene, dinonyl benzene and the like), polyphenyl (e.g., biphenyl, alkylated polyphenyl and the like), polyphenyl ether, alkylated diphenyl ether and diphenyl sulfide, and a derivative therefrom; esters of dibasic acids (e.g., phthalic, succinic, alkyl succinic, alkenyl succinic, maleic, azelaic, suberic, sebacic, fumaric, adipic acids, linolic acid dimer, and the like) and alcohols (e.g., butyl, hexyl, 2-ethylhexyl, dodecyl alcohols, ethylene glycol, diethylene glycol monoether, propylene glycol, and the like); esters of monocarboxylic acids having a carbon number of 5 to 12 and polyols (e.g., neopentyl glycol, trimethylol propane, pentaerythritol, dipentaerythritol, tripentaerytliritol, and the like); and other compounds, such as polyoxyalkylene glycol, polyoxyalkylene glycol ester, polyoxyalkylene glycol ether, phosphoric ester, silicone oil, and the like).

Vegetable base oil includes castor, rapeseed, palm, coconut, olive, sunflower oils and the like.

Lubricant base oil can be prepared by blending base stocks to adjust desired properties, such as viscosity, for specific purposes. For example, it is preferable that a lubricant has a kinematic viscosity of 2 to 30 $mm^2/s$ at 100° C., more preferably 3 to 10 $mm^2/s$, for internal combustion engines, and 2 to 30 $mm^2/s$ at 100°, more preferably 3 to 15 $mm^2/s$, for automatic transmissions.

The lubricant composition of the present invention comprises an adequate quantity of zinc-molybdenum-based dithiocarbamate derivative incorporated into the above base oil. Quantity of the derivative is 1 to 30 mmol per kg of the lubricant composition, preferably 1.5 to 20 mmol/kg, and respective quantities of molybdenum and zinc are 150 to 4000 ppm, preferably 200 to 3000 ppm, and 60 to 3000 ppm, preferably 100 to 2000 ppm, based on the lubricant composition. The derivative may not fully exhibit its effect at a content below 1 mmol/kg, and its effect will no longer reflect an incremental increase in performance relative to the quantity of the derivative at a content above 30 mmol/kg.

The lubricant composition of the present invention can be used for various types of lubricant, such as those for internal combustion engines, automatic transmissions, hydraulic machines, gears, etc. It may be incorporated, as required, with one or more types of adequate additives, such as viscosity index improver, metal-based detergent, ashless dispersant, oxidation inhibitor, extreme pressure agent, anti-wear agent, metal deactivator, pour depressant, corrosion inhibitor, another type of friction modifier, etc.

The viscosity index improver includes polymethacrylate-based, polyisobutylene-based, ethylene/propylene copolymer-based, styrene/butadiene hydrogenated copolymer-based, etc. If present, it is normally contained at 3 to 35% by weight.

The metal-based detergent includes sulfonate, phenate, salicylate and phosphate of an alkali and alkali-earth metal, such as sodium and potassium for the former and calcium, magnesium and barium for the latter. Of these, sulfonate, phenate and salicylate of calcium, magnesium and barium are particularly preferable. If present, it is normally contained at 0.1 to 5% by weight.

The ashless dispersant includes imide alkenylsuccinate and its boron derivative, amide alkenylsuccinate and its boron derivative, benzylamine-based, and succinic acid ester-based. If present, it is normally contained at 0.05 to 7% by weight.

The oxidation inhibitor includes amine-based inhibitors, such as alkylated diphenylamine, phenyl-α-naphthylamine and alkylated phenyl-α-naphthylamine; phenol-based inhibitors, such as 2,6-di-t-butyl phenol and 4,4'-methylenebis-(2,6-di-t-butyl phenol); and zinc dialkyldithiophosphate. If present, it is normally contained at 0.05 to 5% by weight.

The extreme pressure agent includes dibenzyl sulfide and dibutyl disulfide. If present, it is normally contained at 0.05% to 3% by weight.

The antiwear agent includes esters of phosphoric acid, acidic phosphoric acid, phosphorous acid and acidic phosphorous acid. If present, it is normally contained at 0.01 to 5% by weight.

The metal deactivator includes benzotriazole and its derivative, and thiadiazole. If present, it is normally contained at 0.01 to 3% by weight.

The pour depressant includes ethylene/vinyl acetate copolymer, condensate of chlorinated paraffin and naphthalene, condensate of chlorinated paraffin and phenol, polymethacrylate and polyalkylstyrene. If present, it is normally contained at 0.1 to 10% by weight.

Other additives may be freely used, so long as they do not damage the function of the zinc-molybdenum-based dithiocarbamate derivative of the present invention.

Some of the preferred embodiments of the present invention are lubricant composition, comprising:

(1) zinc-molybdenum-based dithiocarbamate derivatives represented by:

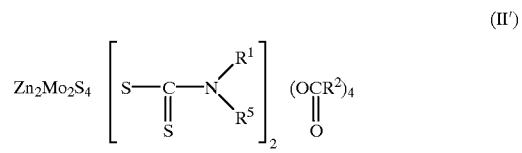

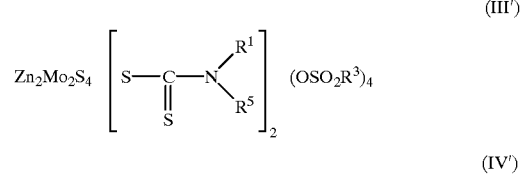

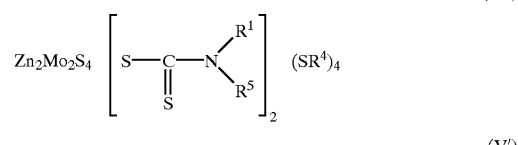

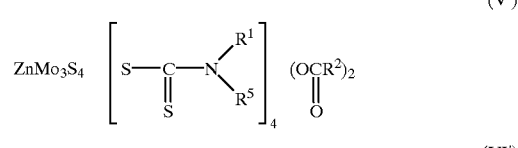

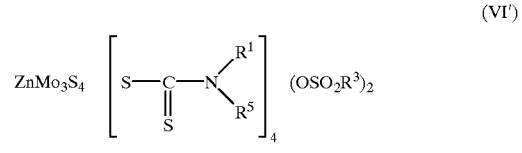

and

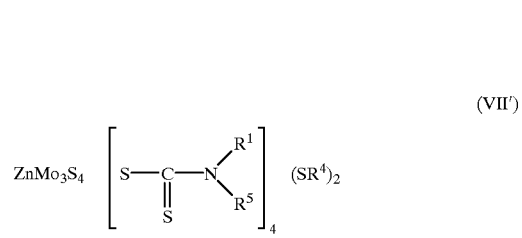

wherein, $R^1$ and $R^5$ are the same or different alkyl groups having a carbon number of 6 to 18, $R^2$ is an alkyl or alkenyl group having a carbon number of 6 to 20, $R^3$ is an alkyl or alkylaryl group having a carbon number of 6 to 30, and $R^4$ is an alkyl group having a carbon number of 6 to 18, (2) a lubricant composition comprising a base oil which contains at least one of the zinc-molybdenum-based dithiocarbamate derivatives represented by general formulae (II') through (VII') at 5 to 30 mmol/kg, and (3) a lubricant composition comprising at least one of the zinc-molybdenum-based dithiocarbamate derivatives represented by general formulae (II') through (VII') incorporated with at least one type of additive selected from a group consisting of viscosity index improver, metal-based detergent, ashless dispersant, oxidation inhibitor, extreme pressure agent, antiwear agent, metal deactivator and pour depressant.

PREFERRED EMBODIMENTS OF THE INVENTION

The present invention is described more concretely by examples and comparative examples.

The base oil used for the examples and comparative examples, and friction/wear test method as the analytical method to assess performance of the lubricant compositions are also described below:

Lubricant Base Oil

Refined (100 neutral oil)(kinematic viscosity: 4.2 mm²/s at 100° C.)

Paraffin lubricant stock: Raffinate from solvent extraction with phenol

Aromatic hydrocarbon content (%CA): 6.0%

Performance Assessment Method

Friction/wear test method

A reciprocating friction tester (SRV friction tester) was used to determine friction coefficient under the following conditions:

Friction material: Steel (SUJ-2)/steel (SUJ-2) cylinder/ disk

Temperature: 80 and 120° C.

Load: 400 N

Frequency: 50 Hz

Test time: 15 minutes

Friction coefficient is an averaged level of the values measured for the last 3 minutes during the test time of 15 minutes. Stability of the coefficient is assessed by the range of its fluctuation.

EXAMPLE 1 (Production of Dinuclide of Mo)

$(NH_4)_2Mo_2S_{12}\cdot 2H_2O$ (13.0 g, 20 mmol) and potassium di(2-ethylhexyl) dithiocarbamate (21.3 g, 60 mmol) were transferred in a nitrogen atmosphere to a 1 L four-mouth flask equipped with a dropping funnel, agitator, thermometer and nitrogen-blowing pipe, to which 300 mL of water was added to dissolve them, and stirred at 60° C. for 8 h while 300 mL of an aqueous solution dissolving 19 g of potassium sulfite was added dropwise over two hours. The product was extracted with 300 mL of ether. The extract was filtered, and the filtrate was subjected to evaporation under a vacuum to remove the ether. The residuum was extracted with 50 mL of methanol three times, and the extract was subjected to evaporation under a vacuum to remove the methanol, to obtain 16.2 g of the following intermediate (1) (yield: 85%).

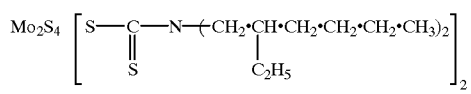

(1)

Zinc chloride (2.72 g, 20 mmol) and the above intermediate (1) (9.53 g, 10 mmol) were transferred to a four-mouth flask, to which 300 mL of a mixed solution of dichloromethane and methanol (50:50 by volume), and stirred for 8 h in a nitrogen atmosphere at room temperature. Next, 100 ML of a methanol solution dissolving 12.8 g (40 mmol) of a potassium salt of oleic acid and then 100 mL of dichloromethane were added to the above, and the mixture was stirred for 24 h at room temperature. It was then subjected to evaporation under a vacuum to remove the dichloromethane and methanol. The residuum was dissolved in 100 mL of hexane, and the solution was filtered. The filtrate was subjected to Sephadex G-10 column chromatography (column inner diameter: 4.5 cm, length: 20 cm) and then treated with 100 mL of hexane. The hexane solution was then subjected to evaporation under a vacuum, to obtain 18.7 g of the following product (yield: 84.8%):

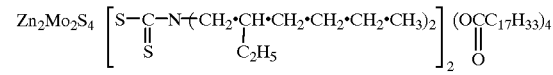

(II-1)

The elementary and ICP analysis results are given below:

Elementary analysis results:

Observed composition

C: 57.6%, H: 9.2%, O: 5.9%, N: 1.3%, S: 11.4%

Theoretical composition

C: 57.6%, H: 9.1%, O: 5.8%, N: 1.3%, S: 11.4%

ICP (inductively coupled rf plasma emission spectroscopy) result

Mo/Zn: 1.0

EXAMPLE 2 (Production of Trinuclide of Mo)

$(NH_4)_2Mo_3S_{13}\cdot 2H_2O$ (15.5 g, 20 mmol) and potassium di(2-ethylhexyl) dithiocarbamate (21.3 g, 60 mmol) were transferred in a nitrogen atmosphere to a 1 L four-mouth flask equipped with a dropping funnel, agitator, thermometer and nitrogen-blowing pipe, to which 300 mL of water was added to dissolve them, and stirred at 60° C. for 8 h while 300 mL of an aqueous solution dissolving 19 g of potassium sulfite was added dropwise over two hours. The product was extracted with 300 mL of ether. The extract was filtered, and the filtrate was subjected to evaporation under a vacuum to remove the ether. The residuum was extracted with 50 mL of methanol three times, and the extract was subjected to evaporation under a vacuum to remove the methanol, to obtain 31.0 g of the following intermediate (2) (yield: 92%).

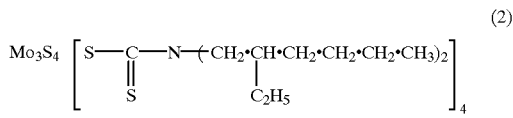

(2)

Zinc chloride (1.36 g, 10 mmol) and the above intermediate (2) (16.8 g, 10 mmol) were transferred to a four-mouth flask, to which 300 mL of a mixed solution of dichloromethane and methanol (50:50 by volume), and stirred for 8 h in a nitrogen atmosphere at room temperature. Next, 100 mL of a methanol solution dissolving 6.4 g (20 mmol) of a potassium salt of oleic acid and then 100 mL of dichloromethane were added to the above, and the mixture was stirred for 24 h at room temperature. It was then subjected to evaporation under a vacuum to remove the dichloromethane and methanol. The residuum was dissolved in 100 mL of hexane, and the solution was filtered. The filtrate was subjected to Sephadex G-10 column chromatography (column inner diameter: 4.5 cm, length: 20 cm) and then treated with 100 mL of hexane. The hexane solution was then subjected to evaporation under a vacuum, to obtain 19.0 g of the following product (yield: 82.0%):

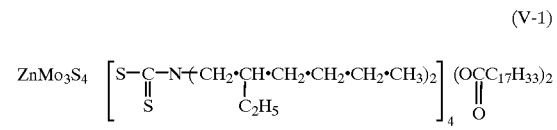

(V-1)

Elementary analysis results:

Observed composition

C: 54.0%, H: 9.0%, O: 2.9%, N: 2.5%, S: 16.2%
Theoretical composition
C: 54.0%, H: 8.8%, O: 2.8%, N: 2.4%, S: 16.6%
ICP result
Mo/Zn: 3.0

EXAMPLE 3 (Production of Dinuclide of Mo)

The intermediate (1) synthesized by EXAMPLE 1 (9.53 g, 10 mmol) and zinc chloride (2.72 g, 20 mmol) were transferred to a four-mouth flask, to which 300 mL of a mixed solution of dichloromethane and methanol (50:50 by volume), and stirred for 8 h in a nitrogen atmosphere at room temperature. Next, 100 mL of a methanol solution dissolving 9.6 g (40 mmol) of a potassium salt of lauryl mercaptan and then 100 mL of dichloromethane were added to the above, and the mixture was stirred for 24 h at room temperature. It was then subjected to evaporation under a vacuum to remove the dichloromethane and methanol. The residuum was dissolved in 100 mL of hexane, and the solution was filtered. The filtrate was subject to Sephadex G-10 column chromatography (column inner diameter: 4.5 cm, length: 20 cm) and then treated with 100 mL of hexane. The hexane solution was then subjected to evaporation under a vacuum, to obtain 15.4 g of the following product (yield: 81.7%):

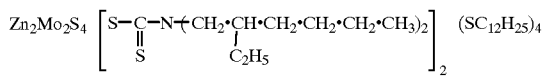

(IV-1)

Elementary analysis results:
Observed composition
C: 52.1%, H: 9.1%, N: 1.6%, S: 20.2%
Theoretical composition
C: 52.1%, H: 9.0%, N: 1.5%, S: 20.4%
ICP result
Mo/Zn: 1.0

EXAMPLE 4 (Production of Trinuclide of Mo)

The same procedure as used for EXAMPLE 3 was repeated, except 16.8 (10 mmol) of the intermediate (2) synthesized by EXAMPLE 2, 1.36 g of zinc chloride and 4.8 g (20 mmol) of a potassium salt of lauryl mercaptan were used to obtain 17.1 g of the following product (yield: 79.6%):

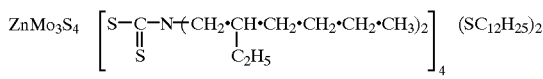

(VII-1)

The elementary and ICP analysis results are given below:
Elementary analysis results:
Observed composition
C: 51.4%, H: 8.8%, N: 2.7%, S: 20.7%
Theoretical composition
C: 51.4%, H: 8.7%, N: 2.6%, S: 20.9%
ICP result
Mo/Zn: 3.0

EXAMPLE 5

A lubricant composition (Sample Oil 1) was prepared by incorporating 2.2 g (1 mmol) of the compound (Compound (I)) obtained by EXAMPLE 1 and represented by formula (II-1) into 197.8 g of 100 neutral oil.

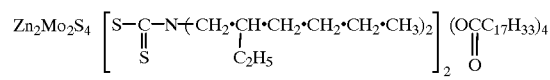

(II-1)

Sample Oil 1, containing 5 mmol/kg of Compound (I), 654 ppm of Zn and 959 ppm of Mo, was analyzed for its performance by the friction/wear test, described earlier. The results are given in Table 1. As shown, it shows a low friction coefficient at 80 and 120° C., and good stability of the coefficient.

EXAMPLE 6

The same procedure as used for EXAMPLE 5, except quantity of the 100 neutral oil was increased from 197.8 to 397.8 g, was repeated to obtain Sample Oil 2. It was analyzed by the friction/wear test. The results are given in Table 1.

EXAMPLE 7

A lubricant composition (Sample Oil 3) was prepared by incorporating 2.31 g (1 mmol) of the compound (Compound (II)) obtained by EXAMPLE 2 and represented by formula (V-1) into 197.6 g of 100 neutral oil.

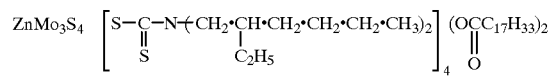

(V-1)

Sample Oil 3, containing 5 mmol/kg of Compound (II), 327 ppm of Zn and 1439 ppm of Mo, was analyzed for its performance by the friction/wear test, described earlier. The results are given in Table 1.

EXAMPLE 8

The same procedure as used for EXAMPLE 7, except quantity of the 100 neutral oil was increased from 197.69 to 397.69 g, was repeated to obtain Sample Oil 4. It was analyzed by the friction/wear test. The results are given in Table 1.

EXAMPLE 9

A lubricant composition (Sample Oil 5) was prepared by incorporating 1.892 g (1 mmol) of the compound (Compound (III)) obtained by EXAMPLE 3 and represented by formula (IV-1) into 198.11 g of 100 neutral oil.

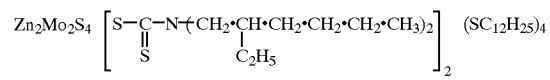

(IV-1)

Sample Oil 5, containing 5 mmol/kg of Compound (III), 654 ppm of Zn and 959 ppm of Mo, was analyzed for its performance by the friction/wear test, described earlier. The results are given in Table 1. As shown, it shows a low friction coefficient at 80 and 120° C., and good stability of the coefficient.

EXAMPLE 10

A lubricant composition (Sample Oil 6) was prepared by incorporating 2.15 g (1 mmol) of the compound (Compound (IV)) obtained by EXAMPLE 4 and represented by formula (VII-1) into 97.85 g of 100 neutral oil.

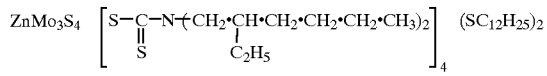

(VII-1)

Sample Oil 6, containing 5 mmol/kg of Compound (IV), 327 ppm of Zn and 1439 ppm of Mo, was analyzed for its performance by the friction/wear test, described earlier. The results are given in Table 1. As shown, it shows a low friction coefficient at 80 and 120° C., and good stability of the coefficient.

EXAMPLE 11

A lubricant composition (Sample Oil 7) was prepared by incorporating 1.66 g (1 mmol) of the compound (Compound (V)) obtained by the same procedure as used in EXAMPLE 1, except a potassium salt of 2-ethylhexoic acid was used in place of a potassium salt of oleic acid, and represented by formula (II-2) into 198.34 g of 100 neutral oil.

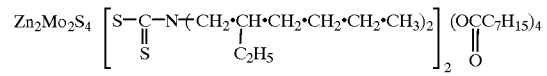

(II-2)

Sample Oil 7, containing 5 mmol/kg of Compound (V), 654 ppm of Zn and 959 ppm of Mo, was analyzed for its performance by the friction/wear test, described earlier. The results are given in Table 1. As shown, it shows a low friction coefficient at 0.03 at 80 and 120° C., and good stability of the coefficient.

EXAMPLE 12

A lubricant composition (Sample Oil 8) was prepared by incorporating 2.03 g (1 mmol) of the compound (Compound (VI)) obtained by the same procedure as used in EXAMPLE 2, except a potassium salt of 2-ethylhexoic acid was used in place of a potassium salt of oleic acid, and represented by formula (V-2) into 197.97 g of 100 neutral oil.

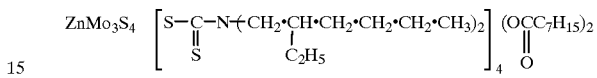

(V-2)

Sample Oil 8, containing 5 mmol/kg of Compound (VI), 327 ppm of Zn and 1439 ppm of Mo, was analyzed for its performance by the friction/wear test, described earlier. The results are given in Table 1.

EXAMPLE 13

A lubricant composition (Sample Oil 9) was prepared by incorporating 2.92 g (1 mmol) of the compound (Compound (VII)) obtained by the same procedure as used in EXAMPLE 1, except a potassium salt of dinonylnaphthalenesulfonic acid was used in place of potassium salt of oleic acid, and represented by formula (III-1) into 197.08 g of 100 neutral oil.

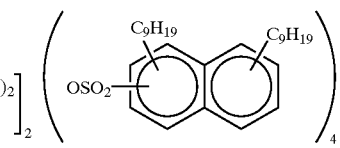

(III-1)

Sample Oil 9, containing 5 mmol/kg of Compound (VI), 654 ppm of Zn and 959 ppm of Mo, was analyzed for its performance by the friction/wear test, described earlier. The results are given in Table 1.

EXAMPLE 14

A lubricant composition (Sample Oil 10) was prepared by incorporating 2.67 g (1 mmol) of the compound (Compound (VII)I) obtained by the same procedure as used in EXAMPLE 2, except a potassium salt of dinonylnaphthalenesulfonic acid was used in place of potassium salt of oleic acid, and represented by formula (V-1) into 197.33 g of 100 neutral oil.

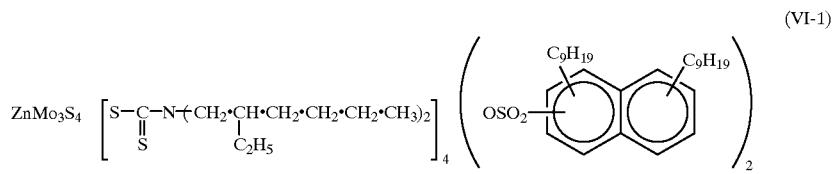

Sample Oil 10, containing 5 mmol/kg of Compound (VI), 327 ppm of Zn and 1439 ppm of Mo, was analyzed for its performance by the friction/wear test, described earlier. The results are given in Table 1.

COMPARATIVE EXAMPLE 1

The base oil of 100 neutral oil as Sample Oil (a) was analyzed for its performance by the friction/wear test, described earlier. The results are given in Table 2. As shown, it has a high friction coefficient, 0.16 at 80° C. and 0.17 at 120° C., and is poor in stability of friction coefficient at 120° C.

COMPARATIVE EXAMPLES 2 AND 3

Sample Oils (b) and (c) were prepared by incorporating 100 neutral oil with respective 250 and 500 ppm (as molybdenum) of MoDTC, and analyzed for their performance by the friction/wear test, described earlier. The results are given in Table 2.

COMPARATIVE EXAMPLE 4

Sample Oil (d) was prepared by the same procedure as used for COMPARATIVE EXAMPLE 3, except MoDTP was used in place of MoDTC, and analyzed for its performance by the friction/wear test, described earlier. The results are given in Table 2.

COMPARATIVE EXAMPLE 5

Sample Oil (e) was prepared by incorporating 100 neutral oil with 500 ppm (as molybdenum) of MoDTC and 1000 ppm (as phosphorus) of ZnDTP, and analyzed for its performance by the friction/wear test, described earlier. The results are given in Table 2. As shown, it has a low friction coefficient of 0.05 and good stability of friction coefficient at 80° C., but a much higher friction coefficient of 0.10 and poor stability of friction coefficient at 120° C., indicating that it has insufficient friction-related characteristics at high temperature.

TABLE 1

|  | EXAMPLE 5 | EXAMPLE 6 | EXAMPLE 7 | EXAMPLE 8 | EXAMPLE 9 | EXAMPLE 10 | EXAMPLE 11 | EXAMPLE 12 | EXAMPLE 13 | EXAMPLE 14 |
|---|---|---|---|---|---|---|---|---|---|---|
|  | Sample Oils | | | | | | | | | |
|  | 1 | 2 | 3 | 4 | 5 | 6 | 7 | 8 | 9 | 10 |
| Base Oil | ← Refined Mineral Oil → | | | | | | | | | |
| Zinc-molybdenum-based, Compounds | | | | | | | | | | |
| Compound (I) mmol/kg | 5 | 2.5 | | | | | | | | |
| Compound (II) mmol/kg | | | 5 | 2.5 | | | | | | |
| Compound (III) mmol/kg | | | | | 5 | | | | | |
| Compound (IV) mmol/kg | | | | | | 5 | | | | |
| Compound (V) mmol/kg | | | | | | | 5 | | | |
| Compound (VI) mmol/kg | | | | | | | | 5 | | |
| Compound (VII) mmol/kg | | | | | | | | | 5 | |
| Compound (VIII) mmol/kg | | | | | | | | | | 5 |
| Performance Assessment | | | | | | | | | | |
| Friction-related Characteristics | | | | | | | | | | |
| 80° C. | | | | | | | | | | |
| Coefficient of Friction | 0.03 | 0.04 | 0.03 | 0.04 | 0.03 | 0.03 | 0.03 | 0.03 | 0.03 | 0.03 |
| Stability of Coefficient of Friction | Good | Good | Good | Good | Good | Good | Good | Good | Good | Good |
| 120° C. | | | | | | | | | | |
| Coefficient of Friction | 0.03 | 0.04 | 0.03 | 0.04 | 0.03 | 0.03 | 0.03 | 0.03 | 0.03 | 0.03 |
| Stability of Coefficient of Friction | Good | Good | Good | Good | Good | Good | Good | Good | Good | Good |

TABLE 1-continued

|  |  | Chemical Formulae |
|---|---|---|
| Compound (I) | $Zn_2Mo_2S_4[(2-EH)_2dtc]_2(OCOC_{17}H_{33})_4$ | II-1 |
| Compound (II) | $ZnMo_3S_4[(2-EH)_2dtc]_4(OCOC_{17}H_{33})_2$ | V-1 |
| Compound (III) | $Zn_2Mo_2S_4[(2-EH)_2dtc]_2(SC_{12}H_{25})_4$ | IV-1 |
| Compound (IV) | $ZnMo_3S_4[(2-EH)_2dtc]_4(SC_{12}H_{25})_2$ | VII-1 |
| Compound (V) | $Zn_2Mo_2S_4[(2-EH)_2dtc]_2(OCOC_7H_{15})_4$ | II-2 |
| Compound (VI) | $ZnMo_3S_4[(2-EH)_2dtc]_4(OCOC_7H_{15})_2$ | V-2 |
| Compound (VII) | $Zn_2Mo_2S_4[(2-EH)_2dtc]_2$ 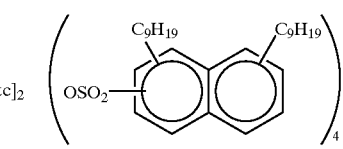 | III-1 |
| Compound (VIII) | $ZnMo_3S_4[(2-EH)_2dtc]_4$ 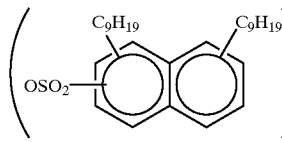 | VI-1 |

TABLE 2

|  | COMPARATIVE EXAMPLE 1 | COMPARATIVE EXAMPLE 2 | COMPARATIVE EXAMPLE 3 | COMPARATIVE EXAMPLE 4 | COMPARATIVE EXAMPLE 5 |
|---|---|---|---|---|---|
|  |  |  | Sample Oils |  |  |
| Base Oil | a | b | c | d | e |
|  |  |  | Refined Mineral Oil |  |  |
| • MoDTC (Mo, ppm) |  | 250 | 500 |  | 500 |
| • MoDTP (Mo, ppm) |  |  |  | 500 |  |
| • ZnDTP (P, ppm) |  |  |  |  | 1000 |
| Performance Assessment |  |  |  |  |  |
| Friction-related Characteristics |  |  |  |  |  |
| 80° C. |  |  |  |  |  |
| Coefficient of Friction | 0.16 | 0.14 | 0.08 | 0.09 | 0.05 |
| Stability of Coefficient of Friction | Good | Good | Good | Good | Good |
| 120° C. |  |  |  |  |  |
| Coefficient of Friction | 0.17 | 0.14 | 0.05 | 0.11 | 0.10 |
| Stability of Coefficient of Friction | Poor | Poor | Poor | Poor | Poor |

MoDTC: sulfided oxymolybdenum di(2-ethylhexyl)dithiocarbamate (Asahi Denka, Sakuralube 100)
MoDTP: sulfided oxymolybdenum di(2-ethylhexyl)dithiophosphate (Asahi Denka, Sakuralube 300)
ZnDTP: zinc di(2-ethylhexyl)dithiophosphate (Oloa, 5660)

The analytical results of the samples prepared by EXAMPLES and COMPARATIVE EXAMPLES show that the zinc-molybdenum-based dithiocarbamate derivative of the present invention as a lubricant additive has a notable friction-reducing effect, because the lubricant composition incorporated with it has a lower friction coefficient and better stability of friction coefficient than the one incorporated with MoDTC or ZnDTP.

What is claimed is:

1. A zinc-molybdenum-based dithiocarbamate represented by general formula (I)

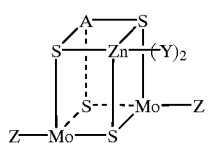

(I)

wherein,

A is Mo—Z or Zn—(—Y)$_2$,

Z in Mo—Z is represented by:

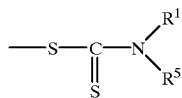

Y in Zn—(—Y)$_2$ is represented by:

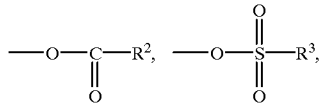

or —SR$^4$, and

R$^1$ to R$^5$ are each a hydrocarbon group having a carbon number of 4 to 30, which may be the same or different.

2. The zinc-molybdenum-based dithiocarbamate derivative of claim 1, represented by general formula (I-1)

  (I-1)

wherein Y is represented by:

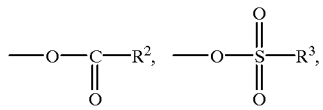

or —SR$^5$, a is 1 or 2, b is 2 or 3, c is 2 or 4, d is 2 when a is 1 or 4 when a is 2, and R$^1$ to R$^5$ are each a hydrocarbon group having a carbon number of 4 to 30.

3. The zinc-molybdenum-based dithiocarbamate derivative of claim 1 or 2, which is a compound selected from a group consisting of the compounds represented by general formulae (II) through (VII):

$$Zn_2Mo_2S_4[SCSN(R^1R^5)]_2(OCOR^2)_4 \quad (II)$$

$$Zn_2Mo_2S_4[SCSN(R^1R^5)]_2(OSO_2R^3)_4 \quad (III)$$

$$Zn_2Mo_2S_4[SCSN(R^1R^5)]_2(SR^4)_4 \quad (IV)$$

$$ZnMo_3S_4[SCSN(R^1R^5)]_4(OCOR^2)_2 \quad (V)$$

$$ZnMo_3S_4[SCSN(R^1R^5)]_4(OSO_2R^3)_2 \quad (VI)$$

and $$ZnMo_3S_4[SCSN(R^1R^5)]_4(SR^4)_2 \quad (VII)$$

wherein, R$^1$ to R$^5$ are each a hydrocarbon group having a carbon number of 4 to 30, which may be the same or different.

4. A method of producing the zinc-molybdenum-based dithiocarbamate derivative of claim 1 or 2 represented by formula (I) or (I-1), comprising stages of:

(a) reaction of sulfurized ammonium molybdate (NH$_4$)$_2$Mo$_2$S$_{12}$.2H$_2$O or (NH$_4$)$_2$Mo$_3$S$_{13}$.2H$_2$O with an alkali metal salt of sulfite and alkali metal salt of dialkyl dithiocarbamate in an aqueous solution, and (b) reaction of the above product with a zinc halide (ZnX) to synthesize Zn$_2$Mo$_2$S$_4$(dtc)$_2$X$_4$ or ZnMo$_3$S$_4$(dtc)$_4$X$_2$, followed by reaction of the halogen portion of the above product with an alkali metal salt of aliphatic acid, sulfonic acid or alkyl thiol, to form a zinc salt of aliphatic acid, sulfonic acid or alkyl thiol.

5. A lubricant additive comprising the zinc-molybdenum-based dithiocarbamate derivative of claim 1 or 2, represented by formula (I) or (I-1).

6. A lubricant composition comprising a lubricant base oil incorporated with the zinc-molybdenum-based dithiocarbamate derivative of claim 1 or 2, represented by formula (I) or (I-1).

* * * * *